United States Patent [19]

Ohi

[11] 3,953,531

[45] Apr. 27, 1976

[54] ALKYLHYDROQUINONE AND PROCESS FOR PRODUCING THE SAME

[75] Inventor: Reiichi Ohi, Minami-ashigara, Japan

[73] Assignee: Fuji Photo Film Co., Ltd., Minami-ashigara, Japan

[22] Filed: Dec. 19, 1974

[21] Appl. No.: 534,393

[30] Foreign Application Priority Data

Dec. 19, 1973 Japan............................ 48-143287

[52] U.S. Cl............................... 260/625; 96/56; 96/109; 260/799; 252/397; 260/820
[51] Int. Cl.².......................................... C07C 39/08
[58] Field of Search............... 260/625, 624, 624 C, 260/621 R

[56] References Cited
UNITED STATES PATENTS

| | | | |
|---|---|---|---|
| 2,455,746 | 12/1948 | Erickson............................ | 260/625 |
| 2,511,193 | 6/1950 | Bean et al........................... | 260/625 |
| 2,722,556 | 11/1955 | Young et al........................ | 260/625 |
| 2,732,300 | 1/1956 | Thirtle et al....................... | 260/625 |
| 3,772,393 | 11/1973 | Hunter et al....................... | 260/625 |

FOREIGN PATENTS OR APPLICATIONS

| | | | |
|---|---|---|---|
| 858,028 | 11/1961 | United Kingdom................ | 260/625 |

Primary Examiner—James O. Thomas, Jr.
Assistant Examiner—W. B. Lone
Attorney, Agent, or Firm—Sughrue, Rothwell, Mion, Zinn & Macpeak

[57] ABSTRACT 2,5-bis-(1',1'-Dimethylbutyl)hydroquinone and a process for the production thereof which comprises reacting hydroquinone with 2-methyl-1-pentene.

1 Claim, No Drawings

ALKYLHYDROQUINONE AND PROCESS FOR PRODUCING THE SAME

BACKGROUND OF THE INVENTION

1. Field of the Invention

The present invention relates to 2,5-bis-(1',1'-dimethylbutyl)hydroquinone and to a process for producing the same.

2. Description of the Prior Art

Alkylhydroquinones are useful as an antioxidant for rubbers. For example, 2,5-di-t-butylhydroquinone has been produced on an industrial scale and is commercially available (refer to *Handbook of Compound Chemicals for Rubber-Plastics*, issued by Rubber Digest Co., 1966, 6, 1). Further, alkylhydroquinones are used as an antifogging agent for silver halide photographic sensitive materials. For example, U.S. Pat. No. 2,728,659 discloses that 2,5-di-n-dodecylhydroquinone is suitable for such a purpose.

However, as described in the above-described *Handbook of Compound Chemicals for Rubber-Plastics*, the blending of di-t-butylhydroquinone with rubber requires a long time, because it has a melting point above 200°C. If a method for reducing the melting point by introducing a substituent having more carbon atoms than the t-butyl group is applied, a good effect can not be obtained in the case of a t-amyl group, because the melting point of such a compound is above 172°C (refer to the above-described *Handbook of Compound Chemicals for Rubber-Plastics*). Further, though rapid blending can be expected using 2,5-bis-(1',1',3',3'-tetramethylbutyl)hydroquinone (melting point: 132°C) which has an alkyl group having more carbon atoms as the substituent, the yield in the production thereof is very low. It is difficult to say whether the compound would be inexpensive even if an improved process for synthesis as described in Japanese Patent Publication 2346/1967 is used.

Further, where an alkylhydroquinone is used by incorporation in silver halide photographic sensitive materials as described in U.S. Pat. No. 2,728,659, there is a serious defect too that crystals easily precipitate because of the high melting point.

SUMMARY OF THE INVENTION

Accordingly, an object of the present invention is to provide an alkylhydroquinone having a low melting point.

Another object of the present invention is to provide a process for producing industrially and inexpensively a pure alkylhydroquinone having a low melting point.

These objects have been attained with 2,5-bis-(1',1'-dimethylbutyl)hydroquinone

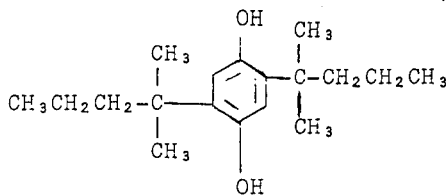

and a process for the production thereof comprising reacting hydroquinone with 2-methyl-1-pentene.

DETAILED DESCRIPTION OF THE INVENTION 2,5-bis-(1',1'-Dimethylbutyl)hydroquinone has a comparatively low melting point (122°C) and can be easily blended in rubber. Further, this compound has the advantage that the tendency toward crystallization thereof is low when it is introduced into silver halide photographic sensitive materials by dissolution in an organic solvent having a high boiling point as used in the conventional method.

According to the present invention, 2,5-bis-(1',1'-dimethylbutyl)hydroquinone can be produced in a high yield by reacting hydroquinone with 2-methyl-1-pentene in the presence of a Lewis acid.

The reaction schematic is as follows.

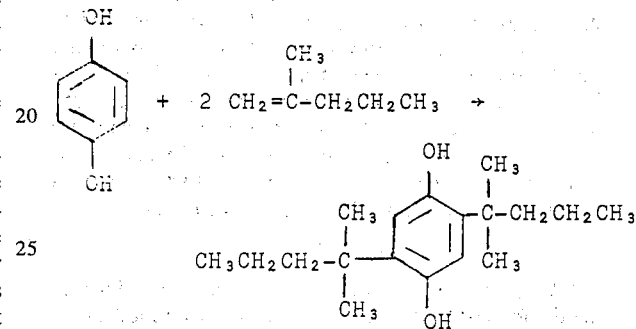

Although it is preferred that hydroquinone and 2-methyl-1-pentene as raw materials have high purity, conventional industrial chemical grades of hydroquinone and 2-methyl-1-pentene are sufficient for use in the present invention.

The molar ratio of the hydroquinone and 2-methyl-1-pentene as the raw materials can range from about 1.5 to 4 moles, preferably 2 to 2.5 moles, of 2-methyl-1-pentene per mole of hydroquinone.

Various compounds known as Lewis acids such as sulfuric acid, phosphoric acid, polyphosphoric acid, zinc chloride, aluminum chloride, boron fluoride or benzene sulfonic acid can be used as the catalyst. While the amount of the catalyst used is not limited, in general, it is preferred to use in an amount of about 10 g to about 200 g of the catalyst per mole of hydroquinone.

As a reaction solvent, all of the solvents conventionally used in Friedel-Crafts reactions using Lewis acids can be employed and those solvents which dissolve hydroquinone well are preferred. Methanol is particularly useful because it is a good solvent for hydroquinone as the raw material. Acetic acid and phosphoric acid are also useful. The amount of the reaction solvent is not limited. In general, a suitable amount of the solvent ranges from about 200 ml to about 1 l per mole of hydroquinone.

In using acetic acid or methanol as the solvent, sulfuric acid is particularly preferred, because it is available at a low price and the reaction proceeds smoothly. A preferred reaction temperature is about 0° to 50°C and particularly preferably 30° to 40°C.

The reaction can be generally carried out in the air, and there is no need to use an inert atmosphere. However, in order to prevent oxidation of hydroquinone an inert atmosphere may be used, if desired.

The reaction time can vary over a very wide range depending on a reaction temperature, amount of the starting materials and other reaction parameters. Usually the reaction time ranges from about 30 minutes to about 10 hours.

Separation of the product can be easily carried out by conventional methods, e.g., by filtration.

According to the process of the present invention, 2,5-bis-(1',1'-dimethylbutyl)hydroquinone can be produced in a high yield. Accordingly, the process of the present invention is an industrially useful process.

The process of the present invention will be illustrated in greater detail by reference to the following examples. Unless otherwise indicated, all parts, percents, ratios and the like are by weight.

EXAMPLE 1

400 ml of methanol was stirred and cooled with ice, and 300 ml of concentrated sulfuric acid was added dropwise thereto. 220 g of hydroquinone was then added thereto with stirring and 370 g of 2-methyl-1-pentene was added dropwise at 30° to 35°C. After the addition, the mixture was stirred at 30 to 35°C for 4 hours. Then, 1 liter of water was added to separate crystals and the separated crystals were filtered. By recrystallization from a solvent mixture of benzene and n-hexane (ratio by volume: 1:3), 450 g of white crystals having a melting point of 122°C was obtained.

EXAMPLE 2

110 g of hydroquinone was dissolved in 1 liter of acetic acid and 100 g of sulfuric acid was added dropwise thereto. 200 g of 2-methyl-1-pentene was added dropwise while the mixture was cooled with ice and the resulting mixture was stirred at 20°C for 5 hours. The reaction mixture was then poured into water and the crystals separated were filtered. After being washed with water, the crystals were washed with n-hexane and dried. Thus, 200 g of white crystals having a melting point of 120°C was obtained.

EXAMPLE 3

110 g of hydroquinone was added to a solution produced by dissolving 400 g of phosphorus pentoxide in 1 kg of phosphoric acid. 200 g of 2-methyl-1-pentene was added dropwise at 40°C and the resulting mixture was stirred at 40°C for 6 hours. The reaction mixture was poured into water and the crystals separated were filtered. After being washed with water, the crystals were washed with n-hexane and dried. Thus, 180 g of white crystals having a melting point of 120°C was obtained.

While the invention has been described in detail and with reference to specific embodiments thereof, it will be apparent to one skilled in the art that various changes and modifications can be made therein without departing from the spirit and scope thereof.

What is claimed is:

1. 2,5-bis-(1',1'-Dimethylbutyl)hydroquinone.

* * * * *